United States Patent [19]

Sze

[11] 3,949,010

[45] Apr. 6, 1976

[54] PRODUCTION OF CHLORINATED HYDROCARBONS

[75] Inventor: Morgan C. Sze, Upper Montclair, N.J.

[73] Assignee: The Lummus Company, Bloomfield, N.J.

[22] Filed: Apr. 8, 1974

[21] Appl. No.: 458,654

[52] U.S. Cl...... 260/654 R; 260/654 A; 260/656 R; 260/659 R; 260/659 A; 260/660; 260/662 R; 260/662 A
[51] Int. Cl.² ........................................ C07C 21/00
[58] Field of Search............ 260/659 R, 659 A, 660, 260/654 H, DIG. 42, 654 R, 654 A, 656 R

[56] References Cited
UNITED STATES PATENTS

| | | | |
|---|---|---|---|
| 2,407,828 | 9/1946 | Gorin | 260/DIG. 42 |
| 2,498,552 | 2/1950 | Kilgren et al. | 260/659 A |
| 3,548,016 | 12/1970 | Sze | 260/659 R |

FOREIGN PATENTS OR APPLICATIONS

| | | | |
|---|---|---|---|
| 711,287 | 6/1965 | Canada | 260/659 A |

Primary Examiner—Delbert E. Gantz
Assistant Examiner—Joseph A. Boska
Attorney, Agent, or Firm—Marn & Jangarathis

[57] ABSTRACT

Oxidized molten chloride salts are employed for chlorinating and/or oxychlorinating a feed in a first reactor and then passed by gravity to a second reactor situated below the first reactor and operated at a pressure higher than the first reactor wherein the molten salt is oxidized. The oxidized salt is returned to the first reactor. Vinyl chloride or chloromethanes can be produced by the process.

10 Claims, 1 Drawing Figure

U.S. Patent   April 6, 1976   3,949,010
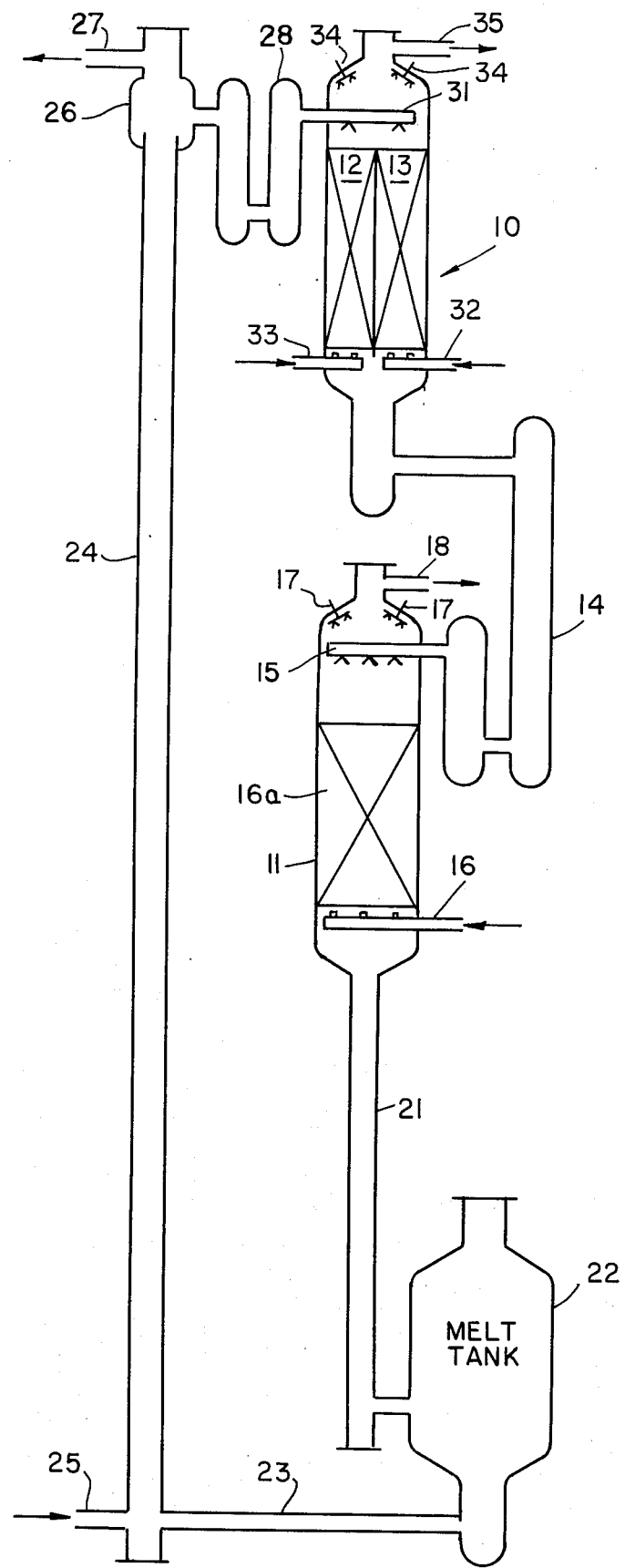

PRODUCTION OF CHLORINATED HYDROCARBONS

The present invention relates to the production of chlorinated hydrocarbons, and more particularly to the production of chlorinated hydrocarbons by the use of molten salts.

The use of molten salts; in particular, copper chlorides for the production of chlorinated hydrocarbons has been previously described in, for example, U.S. Pat. No. 2,407,828 to Gorin; Canadian Pat. No. 711,287 to Bender et al; and Canadian Pat. No. 705,925 to Bender et al.

In U.S. application Ser. No. 688,724 filed on Dec. 8, 1967, and now abandoned, there is described a process for producing vinyl chloride by the use of molten salts wherein the various reactions are effected in a single reactor divided into different zones.

An object of the present invention is to provide an improved process for producing chlorinated hydrocarbons by the use of molten salts.

Another object of the present invention is to provide an improved process for producing vinyl chloride.

A further object of the present invention is to provide an improved process for producing chlormethanes.

These and other objects of the present invention should become apparent from reading the following description of the invention.

In accordance with the present invention, chlorination (oxychlorination) of a hydrocarbon or chlorinated hydrocarbon feed is effected in a first reactor by direct contact with hydrogen chloride and/or chlorine and a molten mixture containing a multivalent metal chloride in its higher and lower valence state and the oxychloride of the multivalent metal to produce an effluent containing chlorinated hydrocarbon. The molten salt is withdrawn from the first reactor and passed, by gravity, to a second reactor (oxidation reactor) below the first reactor wherein the molten salt is directly contacted with molecular oxygen to produce the oxychloride. The molten salt is withdrawn from the second reactor and passed to the first reactor.

In accordance with a preferred embodiment of the present invention, the second reactor (oxidation reactor) is operated at a pressure higher than the first reactor (chlorination and/or oxychlorination reactor).

The melt contains a chloride of a multivalent metal; i.e., a metal having more than one positive valence state, such as manganese, iron, copper, cobalt, and chromium, preferably copper. In the case of higher melting multivalent metal chlorides, such as copper chlorides, a metal salt melting point depressant which is non-volatile and resistant to the action of oxygen at the process conditions, such as a chloride of a univalent metal, i.e., a metal having only one positive valence state is added to the multivalent metal chloride to form a molten salt mixture having a reduced melting point. The univalent metal chlorides, are preferably alkali metal chlorides, such as potassium and lithium chloride in particular, but it is to be understood that other metal chlorides and mixtures thereof, such as the heavy metal chlorides; i.e., heavier than copper, of Groups I, II, III and IV of the Periodic Table; e.g., zinc, silver, and thallium chloride, may also be employed. The metal chloride melting point depressant is added in any amount sufficient to maintain the salt mixtures as a melt at the reaction temperatures, and is generally added in an amount sufficient to adjust the melting point of the molten salt mixture to a temperature of below about 500°F. In the case of a salt mixture of copper chlorides and potassium chloride, the composition of the melt ranges between about 20% and about 40%, preferably about 30%, by weight, potassium chloride, with the remainder being copper chlorides. It is to be understood, however, that in some cases the catalyst melt may have a melting point higher than 500°F., provided the catalyst remains in the form of the melt throughout the processing steps. It is further to be understood that the melt may contain a mixture of multivalent metal chlorides or other reaction promoters. It is also to be understood that in some cases, metal chloride may be maintained as a melt without the addition of a univalent metal halide.

In accordance with the present invention, the oxidation reactor is operated at a pressure which is higher than the operating pressure of the chlorination (oxychlorination) reactor. In general, the oxidation reactor is operated at a pressure of at least about 50 psig, with the pressure generally being from about 50 to about 100 psig. It is to be understood that pressures in excess of 100 psig could be employed, but in general no added beneficial results are obtained by the use of such higher pressures and, accordingly, operation at such higher pressures is not preferred. The chlorination reactor is generally operated at a pressure from about atmospheric pressure up to about 50 psig, preferably a pressure from about 15 to about 50 psig. Higher pressures could be employed, but in general, there is no economic justification for the use of such higher pressures. In general, the oxidation reactor is operated at a pressure which is at least about 10 psig higher, and preferably at least 20 psig higher than the operating pressure of the chlorination reactor.

The oxidation of the melt to generate oxychloride is generally effected at a temperature from about 600°F to about 1000°F and preferably at a temperature from about 700° to about 950°F. The residence time is generally in the order of 1 to about 100 seconds but as should be apparent to those skilled in the art shorter or longer residence times may be employed.

The chlorination (oxychlorination) reactor is generally operated at a temperature from about 600° to about 1000°F, with the exact temperature being dependent upon the feed to the chlorination reactor. In general, the residence time is in the order of 1 to about 100 seconds, but as should be apparent to those skilled in the art, shorter or longer residence times could be employed.

The feed to the melt chlorination (oxychlorination) may be either a hydrocarbon or partially chlorinated hydrocarbon and as representative examples of such feeds, there may be mentioned: aromatic hydrocarbons, such as benzene, aliphatic hydrocarbons (saturated and/or olefinically unsaturated), preferably a $C_1$ to $C_4$ hydrocarbon; or a partially chlorinated derivative of such aromatic and aliphatic hydrocarbons. The most preferred feeds are: ethane, ethylene, methane and partially chlorinated $C_1$ & $C_2$ hydrocarbons.

The present invention is particularly applicable to the production of chlorinated methanes from methane, as described in application Ser. No. 299,114 filed on Oct. 19, 1972 and application Ser. No. 299,848 filed on Oct. 24, 1972; and the production of vinyl chloride from ethane and/or ethylene, as described, for example, in application Ser. No. 153,374 filed on June 15, 1971, all of which are hereby incorporated by reference.

In the production of chlorinated methanes, the chlorination reactor is generally operated at a temperature from about 700° to about 950°F, and preferably at a temperature from about 800° to about 860°F. As disclosed in the aforementioned U.S. applications, the feed to the chlorination (oxychlorination) reaction generally also includes recycle chlorinated methane(s).

In the production of vinyl chloride from ethane and/or ethylene, the chlorination (oxychlorination) reactor is operated at a temperature from about 700° to about 1000°F, preferably a temperature from about 750° to about 950°F, and most preferably at a temperature from about 800° to about 900°F. The feed to the chlorination reactor generally also includes recycle components; in particular, ethyl chloride, ethylene and unreacted ethane in the case where ethane is used as fresh feed.

The effluent from the chlorination reactor also includes dichloroethane; in particular 1,2-dichloroethane, with the effluent also including some quantities of 1,1-dichloroethane. The 1,2-dichloroethane is recovered and dehydrochlorinated to vinyl chloride. The dehydrochlorination can be effected by conventional thermal or catalytic procedures. Alternatively, and preferably, the dehydrochlorination is effected by direct contact with a molten salt containing the higher and lower valent multivalent metal chloride, and generally also the oxychloride.

In accordance with the present invention, the dehydrochlorination of 1,2-dichloroethane and chlorination (oxychlorination) of ethane and/or ethylene feed is effected in a single reactor divided into two sections, one of which is employed for the chlorination (oxychlorination), and the other of which is employed for the dehydrochlorination of 1,2-dichloroethane. The melt from both sections is passed, by gravity, to the oxidation reactor situated below the reactor which is employed for effecting both chlorination and dehydrochlorination. Similarly, the melt withdrawn from the oxidation reactor is introduced into both sections of the chlorination-dehydrochlorination reactor.

The invention will now be further described with respect to specific embodiments thereof illustrated in the accompanying drawing wherein:

The drawing is a simplified schematic representation of an embodiment of the present invention.

Referring now to the drawing, there is illustrated a chlorination (oxychlorination) reactor 10 and an oxidation reactor 11 situated below the chlorination reactor 10. As hereinabove described, reactor 11 is operated at a pressure higher than reactor 10. As particularly shown, the reactor 10 is divided into two sections 12 and 13 whereby the chlorination reactor 10 functions, as hereinafter described, as both a chlorination and dehydrochlorination reactor. The reactor 10, however, is generally referred to as a chlorination reactor, even through the reactor is employed for effecting, in separate sections, both chlorination (oxychlorination) and dehydrochlorination.

Molten salt, preferably a mixture of cuprous and cupric chloride and, as a melting point depressant, potassium chloride, in a seal leg 14, which functions to pass molten salt from reactor 10 to reactor 11 while preventing flow of gas therebetween, is introduced into reactor 11 through a suitable liquid distributor, schematically indicated as 15. The reactor 11 includes suitable means, such as packing, schematically indicated as 16a, for increasing gas-liquid contact in reactor 11.

A compressed oxygen containing gas, such as air, is introduced into the bottom of reactor 11 through a suitable gas distributor, schematically indicated as 16. The gas feed through distributor 16 may also include the combustion products of by-product chlorinated hydrocarbons, including hydrogen chloride, chlorine, water vapor, carbon oxides, nitrogen, as described in application Ser. No. 95,030 filed on Dec. 4, 1970, now U.S. Pat. No. 3,879,481. As a result of the countercurrent contact between the gas introduced through distributor 16 and the molten salt introduced through distributor 15, the molten salt is oxidized to produce oxychloride; in particular, copper oxychloride. In addition, any hydrogen chloride and chlorine are absorbed by the molten salt to generate cupric chloride.

An effluent gas rises to the top of reactor 11 wherein the effluent may be quenched by direct contact with a suitable quench liquid, such as aqueous hydrogen chloride, introduced through quency nozzles 17. The effluent gas is withdrawn from reactor 11 through pipe 18 for further treatment as disclosed in the hereinabove referred to U.S. patent applications.

The oxidized molten salt is withdrawn from reactor 11 through pipe 21 and flows therethrough to a melt storage tank 22. The molten salt passes from melt storage tank 22 through pipe 23 into gas lift pipe 24 wherein the molten salt is lifted by a suitable lift gas, introduced through pipe 25, into a melt separation vessel 26. The temperature of the molten salt may be suitably regulated by regulating the temperature of the lift gas introduced through pipe 25. A suitable lift gas for use in lift pipe 24 would be the essentially nitrogen containing gas which is derived from the gaseious effluent withdrawn from reactor 11, as described in the aforementioned U.S. Pat. applications.

The melt and lift gas are separated in vessel 26 with the lift gas being withdrawn therefrom through line 27. The molten salt is passed from vessel 26 through seal leg 28 and introduced into the top portion of reactor 10 through a suitable liquid distributor, schematically indicated as 31. The vessel 10 is provided with suitable means for promoting gas-liquid contact, such as packing. As hereinabove described the vessel 10 is divided into separate reaction sections 12 and 13, and the liquid distributor 31 introduces molten salt into both of the sections 12 and 13.

As particularly described section 12 is employed for the dehydrochlorination of 1,2-dichloroethane produced by chlorination (oxychlorination) of ethane and/or ethylene, and section 13 is employed for chlorination (oxychlorination) of fresh feed.

Fresh feed ethane and/or ethylene, recycle components; in particular, ethyl chloride, ethylene and unreacted ethane, and hydrogen chloride and/or chlorine are introduced into section 13 of reactor 10 through a suitable gas distributor, schematically indicated as 32 and is countercurrently contacted with the oxidized molten salt.

1,2-dichloroethane is introduced into section 12 of reactor 10 through a suitable gas distributor, schematically indicated as 33 wherein the 1,2-dichloroethane is countercurrently contacted with molten salt to effect dehydrochlorination thereof. As described in the aforementioned U.S. patent applications, the hydrogen chloride generated during dehydrochlorination reacts with the oxychloride of the molten salt.

The effluents from reaction sections 12 and 13 are combined in the top of reactor 10 and may be quenched by a suitable quench liquid; such as, heavier chlorinated hydrocarbons, introduced through quench nozzles. The gaseous effluent is withdrawn from reactor 10 through outlet pipe 35 and passed to a separation and recovery section (not shown) for recovery of various components, as described, for example, application Ser. No. 153,374. As described therein, 1,2-

The chlorination reactor feeds and effluent are as tabulated in Table I.

The molten salt streams circulating in the chlorinator and oxidizer vessels are as tabulated in Table II.

The use of an oxidizer operating pressure of 60 psig, requires about 60% of the packing volume or contacting surface area which would be required at 30 psig.

TABLE I

|  | Chlorine Feed | | Fresh Methanol Feed | | Recycle $CH_4$ Feed | | HCl Feed | | Reactor Effluent | |
|---|---|---|---|---|---|---|---|---|---|---|
|  | M/Hr | lb/Hr | M/Hr | lb/Hr | M/Hr | lb/Hr | M/Hr | lb/Hr | M/Hr | lb/Hr |
| $CH_4$ |  |  | 72.17 | 1154.7 | 168.4 | 2694.4 |  |  | 169.4 | 2710.4 |
| $C_2H_6$ |  |  | 0.14 | 4.2 | 0.08 | 2.3 |  |  | 0.08 | 2.3 |
| $H_2$ | 0.16 | 0.3 |  |  |  |  |  |  |  |  |
| $N_2$ | 0.31 | 8.7 | 0.04 | 1.1 | 8.50 | 238.0 | 0.22 | 6.2 | 9.22 | 258.2 |
| $O_2$ | 0.08 | 2.6 |  |  |  |  |  |  |  |  |
| $Cl_2$ | 38.40 | 2700.8 |  |  |  |  |  |  |  |  |
| CO |  |  |  |  | 1.40 | 39.2 |  |  | 1.60 | 44.8 |
| $CO_2$ | .24 | 10.6 |  |  | 1.0 | 44 | 0.17 | 7.5 | 6.21 | 273.2 |
| $CH_3Cl$ |  |  |  |  | 4.5 | 227.3 |  |  | 42.46 | 2144.2 |
| $CH_2Cl_2$ |  |  |  |  | 0.1 | 8.5 |  |  | 19.91 | 1692.4 |
| $CHCl_3$ |  |  |  |  |  |  |  |  | 7.22 | 862.8 |
| $CCl_4$ |  |  |  |  |  |  |  |  | 1.18 | 181.7 |
| $C_2$Chlorohydrocarbons |  |  |  |  |  |  |  |  | .15 | 18.7 |
| HCl |  |  |  |  |  |  | 26.80 | 980 | 1.50 | 54.8 |
| $H_2O$ |  |  |  |  |  |  |  |  | 74.90 | 1348.0 |
| Total | 39.19 | 2723 | 72.35 | 1160 | 184.0 | 3253.7 | 27.19 | 993.7 | 333.83 | 9591.5 | dichloroethane is recovered for introduction into reactor section 12; vinyl chloride is recovered as net product; and ethane, ethylene and ethyl chloride are recovered for recycle to reaction section 13.

Molten salt is withdrawn from reactor 10 through outlet pipe 37 and passed, by gravity, through seal leg 14 for introduction into reactor 11.

It is to be understood that although the invention has been particularly described with respect to the production of vinyl chloride the invention is equally applicable to the production of other chlorinated derivatives, and in particular, to the production of chloromethanes. In the production of chloromethanes, reactor 10 is not divided into two sections and methane and recycle chloromethane(s) are introduced into reactor 10.

Similarly, vinyl chloride could be produced by the use of only a single section in reactor 10. In such a case, dichloroethane is dehydrochlorinated in a separate vessel either thermally, catalytically or by the use of molten salts.

Furthermore, although the oxidizer and chlorination reaction zones are particularly described as two separate vessels, such zones could be maintained as separate and distinct zones in a single vessel.

The above modifications and others should be apparent to those skilled in the art from the teachings herein.

The present invention will be further described with respect to the following example, but it is to be understood that the scope of the invention is not to be limited thereby.

EXAMPLE

Molten salt as reported in Table II is circulated between oxidation reactor 11 and chlorination reactor 10. The process is directed to the production of chloromethanes and, accordingly, reactor 10 is not divided into two zones. The chlorination reactor is operated at an average temperature of 820°F and a pressure of 30 psig and the oxidation reactor is operated at an average temperature of 820°F and a pressure of 60 psig. Air is fed to the oxidation reactor at a rate of 237.2 M/hr (6199.6 lb/hr.)

TABLE II

|  | Salt to Oxidizer | | Salt to Chlorinator | |
|---|---|---|---|---|
|  | M/Hr | lb/Hr | M/Hr | lb/Hr |
| KCl | 3150 | 234700 | 3150 | 234700 |
| CuCl | 2370 | 234630 | 2195 | 217305 |
| $CuCl_2$ | 2230 | 299935 | 2232 | 300204 |
| $CuO.CuCl_2$ |  |  | 86.5 | 18511 |
|  |  | 769265 |  | 770720 |

The present invention is particularly advantageous in that by using stacked reactors molten salt can be transferred between the reactors by the use of only one gas lift. Furthermore, the use of a higher operating pressure in the oxidation reactor improves the rate of oxidation and permits the use of smaller contacting bed volumes. On the other hand, an increase in the pressure of the chlorination reactor does not significantly decrease the required contact bed volume and, accordingly, the chlorination reactor is operated at a pressure lower than that employed in the oxidation reactor. Accordingly, by using stacked reactors with the oxidation reactor being operated at a pressure higher than and situated below the chlorination (oxychlorination) reactor, there is an improvement in the economics of the overall process.

Numerous modifications and variations of the present invention are possible in light of the above teachings and, therefore, within the scope of the appended claims the invention may be described otherwise than as particularly described.

What is claimed:

1. A process for producing a chlorinated hydrocarbon comprising:
    contacting in a first reaction zone a hydrocarbon and a member selected from the group consisting of chlorine, hydrogen chloride and mixtures thereof, with a molten salt mixture comprising the higher and lower valent chlorides of a multivalent metal and the oxychloride of the metal; said first reaction zone being operated at a pressure of from 15 to 50 psig;

recovering chlorinated hydrocarbon from the first reaction zone;

passing molten salt from the first reaction zone to a second reaction zone positioned below the first reaction zone; contacting the salt mixture in the second reaction zone with molecular oxygen to generate oxychloride, said second reaction zone being operated at a pressure of at least 50 psig and at least 10 psig greater than the pressure in the first reaction zone; and passing molten salt mixture from the second reaction zone to the first reaction zone.

2. The process of claim 1 wherein the first and second reaction zones are operated at a temperature from about 600°F to about 1000°F.

3. The process of claim 2 wherein the molten salt mixture in the first reaction zone comprises cuprous chloride, cupric chloride and copper oxychloride.

4. The process of claim 1 wherein the molten salt mixture in the first reaction zone comprises cuprous chloride, cupric chloride and copper oxychloride.

5. The process of claim 4 wherein the hydrocarbon is methane.

6. The process of claim 5 wherein the first reaction zone is operated at a temperature from about 700° to about 950°F and the second reaction zone is operated at a temperature from about 600° to about 1000°F.

7. The process of claim 6 wherein the first reaction zone is operated at a pressure from about 15 to about 50 psig and the second reaction zone at a pressure from about 50 to about 100 psig.

8. The process of claim 4 wherein the hydrocarbon is selected from the groups consisting of ethane, ethylene and mixtures thereof.

9. The process of claim 8 wherein the first reaction zone is operated at a temperature from about 700° to about 1000°F and the second reaction zone is operated at a temperature from about 600° to about 1000°F.

10. The process of claim 9 wherein the first reaction zone is operated at a pressure from about 15 to about 50 psig and the second reaction zone at a pressure from about 50 to about 100 psig.

* * * * *

UNITED STATES PATENT OFFICE
CERTIFICATE OF CORRECTION

Patent No. 3,949,010          Dated April 6, 1976

Inventor(s) Morgan C. Sze

It is certified that error appears in the above-identified patent and that said Letters Patent are hereby corrected as shown below:

Column 1, line 25, "chlormethanes" should be -- chloromethanes --.

Column 3, line 57, "through" should be -- though --.

Column 4, line 33, "gaseious" should be -- gaseous --.

Columns 5 and 6, Table I, in the heading, "Fresh Methanol Feed" should be -- Fresh Methane Feed --.

Signed and Sealed this

Twenty-sixth Day of October 1976

[SEAL]

Attest:

RUTH C. MASON
*Attesting Officer*

C. MARSHALL DANN
*Commissioner of Patents and Trademarks*